United States Patent [19]
Anderson
[11] Plant 4,792
[45] Nov. 17, 1981

[54] NECTARINE TREE

[76] Inventor: Frederic W. Anderson, 826 W. 22nd St., Merced, Calif. 95340

[21] Appl. No.: 189,214

[22] Filed: Sep. 22, 1980

[51] Int. Cl.³ ..... A01H 5/03
[52] U.S. Cl. ..... Plt./41
[58] Field of Search ..... Plt./41

*Primary Examiner*—Robert E. Bagwill
*Attorney, Agent, or Firm*—Roger B. Webster

[57] ABSTRACT

A nectarine tree which is large-medium size, spreading, dense, foliated with medium size, lanceolate, acutely pointed leaves having a crenate margin and alternate, reniform glands, blooms from medium size buds and with large flowers about with the Aurelio Grand, and is regular and very productive bearer of early-season, uniform, medium size, symmetrical, globose, freestone fruit having yellow skin overspread with red, yellow flesh, and a medium size, beige stone.

1 Drawing Figure

CLASSIFICATION OF THE VARIETY

The present variety of nectarine tree is embraced by Class 41, Plants, of the U.S. Patent Office Manual of Classification.

BACKGROUND OF THE VARIETY

1. Field of the Invention

Over a substantial number of years I have engaged in an extensive and continuing plant breeding program to my experimental nursery and orchard located near Le Grand, Merced County, Calif.; one purpose of such program being to provide improved varieties of fruit trees. The present variety of nectarine tree resulted from my endeavors in the conduct of such plant breeding program.

2. Prior Varieties

Among the existent varieties of nectarine tree which are known to me, I make particular reference to the Aurelio Grand (U.S. Plant Pat. No. 3,755) as mentioned hereinafter in this specification.

Origin of the variety: The present variety of nectarine tree was originated by me, in my experimental nursery and orchard located as aforesaid, as an open-pollinated seedling of the Aurelio Grand; a number of such seedlings having been grown under careful and continuing observation. The present variety was selected by me from such seedlings upon evidencing desirable characteristics for commercial production.

Asexual reproduction of the variety: Subsequent to origination and selection by me of the present variety of nectarine tree, I asexually reproduced it by budding on older seedlings, and—in maturity—such reproductions ran true to the original tree in all respects.

Summary of the variety: The herein-claimed variety of nectarine tree is large-medium size, spreading, dense, foliated with medium size, lanceolate, acutely pointed leaves having a crenate margin and alternate, reniform glands, blooms from medium size buds and with large flowers about with the Aurelio Grand, and is a regular and very productive bearer of early-season, uniform, medium size, symmetrical, globose, freestone fruit having yellow skin overspread with red, yellow flesh, and a medium size, beige stone.

The herein-claimed variety is further characterized by early-season, freestone fruit which—while generally similar to the Aurelio Grand—is somewhat larger, firmer of flesh, and ripens two to three days later—thus extending the harvest period for fruit of the Aurelio Grand type.

BRIEF DESCRIPTION OF THE DRAWING

The drawing is an illustration, by photographic reproduction in color, of leaves of the variety and separate fruit; one fruit being cut away to expose the flesh and stone.

DESCRIPTION OF THE VARIETY

The botanical details of this new and distinct variety of nectarine tree—with color definitions (except those in common color terms) referenced to Maerz and Paul Dictionary of Color—are as follows:

Tree:
- *Size.*—Large — medium.
- *Growth.*—Spreading.
- *Density.*—Dense.
- *Production.*—Very productive.
- *Bearing.*—Regular bearer.

Trunk:
- *Size.*—Medium.

Branches:
- *Size.*—Medium.

Leaves:
- *Size.*—Medium. Average length — $5\frac{3}{4}''$. Average width — $1\frac{3}{8}''$.
- *Form.*—Lanceolate. Acutely pointed.
- *Color.*—Top side — medium green (23-L-10). Under side — lighter green (22-I-6).
- *Margin.*—Crenate.
- *Petiole.*—Medium length — average $\frac{1}{2}''$.
- *Glands.*—Average number — 3. Green. Alternate. Reniform. Position — usually 1 or 2 on petiole and 1 or more on base of blade.

Flower buds:
- Size.—Medium.

Flowers:
- *Blooming period.*—About with Aureolio Grand. Medium, as compared with other varieties.
- *Size.*—Large.

*Fruit:*
- *Maturity when described.*—Hard.
- *Ripening period.*—2 or 3 days after Aurelio Grand.

*Size.*—Uniform. Medium. Average diameter axially — $2\frac{3}{8}''$. Average transversely in suture plane — $2\frac{3}{8}''$.

*Form.*—Uniform. Symmetrical.. Globose.

*Suture.*—Shallow.

*Cavity.*—Rounded. Circular.

*Base.*—Rounded.

*Apex.*—Short.

Skin:

*Thickness.*—Medium.

*Tendency to crack.*—None noted.

*Color.*—Yellow (9-L-6) overspread with red (5-L-5) shading to darker red (8-L-6).

Flesh:

*Color.*—Yellow (10-L-3). Surface of pit cavity: yellow.

*Texture.*—Firm. Fine. Crisp.

*Ripens.*—Evenly.

*Flavor.*—Subacid.

*Aroma.*—Distinct.

*Eating quality.*—Good.

Stone:

*Type.*—Free.

*Size.*—Medium. Average length — $1\frac{3}{8}''$. Average breadth — $1''$. Average thickness — $\frac{7}{8}''$.

*Form.*—Oblong.

*Tendency to split.*—Slight.

*Color.*—Beige (13-I-7).

Use: Market. Dessert. Long distance shipping.

Keeping quality: Good.

Resistance to insects and diseases: No unusual susceptibilities noted.

Shipping quality: Good.

The nectarine tree and its fruit herein described may vary in slight detail due to climatic and soil conditions under which the variety may be grown; the present description being of the variety as grown in the Central Valley of California.

I claim:

1. A new and distinct variety of nectarine tree, substantially as illustrated and described, characterized by early, regular, and very productive bearing of freestone fruit which—while generally similar to the Aurelio Grand—is somewhat larger, firmer of flesh, and ripens two to three days later.

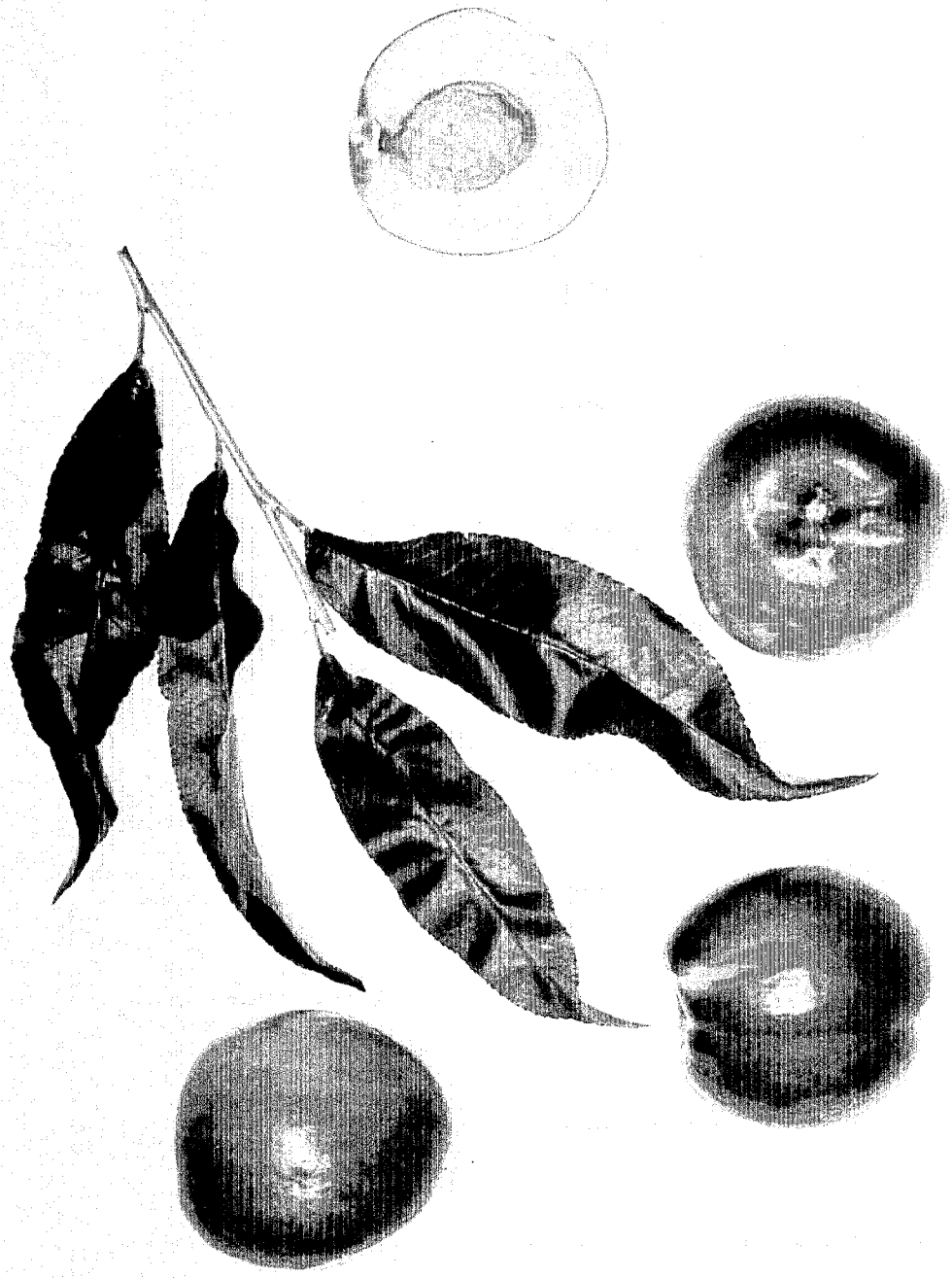

* * * * *